US008623634B2

(12) United States Patent
Yanik et al.

(10) Patent No.: US 8,623,634 B2
(45) Date of Patent: Jan. 7, 2014

(54) GROWING AQUATIC BIOMASS, AND PRODUCING BIOMASS FEEDSTOCK AND BIOCRUDE THEREFROM

(75) Inventors: Steve Yanik, Colorado Springs, CO (US); Robert Bartek, Centennial, CO (US)

(73) Assignee: KiOR, Inc., Pasadena, TX (US)

( * ) Notice: Subject to any disclaimer, the term of this patent is extended or adjusted under 35 U.S.C. 154(b) by 572 days.

(21) Appl. No.: 12/818,846

(22) Filed: Jun. 18, 2010

(65) Prior Publication Data

US 2011/0023565 A1  Feb. 3, 2011

Related U.S. Application Data

(60) Provisional application No. 61/219,562, filed on Jun. 23, 2009.

(51) Int. Cl.
*C12N 1/00* (2006.01)
*C12N 13/00* (2006.01)
*C10B 57/04* (2006.01)

(52) U.S. Cl.
USPC .............. 435/257.1; 435/173.1; 201/25

(58) Field of Classification Search
USPC .................. 44/307; 47/1.4; 71/11; 422/187; 435/277.1; 210/602; 705/39
See application file for complete search history.

(56) References Cited

U.S. PATENT DOCUMENTS

| | | | |
|---|---|---|---|
| 3,961,913 A | 6/1976 | Brenneman et al. | |
| 4,064,018 A | 12/1977 | Choi | |
| 4,147,593 A | 4/1979 | Frischmuth et al. | |
| 4,153,514 A | 5/1979 | Garrett et al. | |
| 4,266,083 A | 5/1981 | Huang | |
| 4,308,411 A | 12/1981 | Frankiewicz | |
| 4,711,873 A | 12/1987 | Suzukamo et al. | |
| 4,851,601 A | 7/1989 | Fukuda et al. | |
| 4,874,507 A | 10/1989 | Whitlock | |
| 4,987,114 A | 1/1991 | Suzukamo et al. | |
| 5,064,527 A | 11/1991 | Singhal et al. | |
| 5,097,088 A | 3/1992 | Fukao et al. | |
| 5,102,628 A | 4/1992 | De Lasa | |
| 5,115,084 A | 5/1992 | Himmelblau | |
| 5,233,109 A | 8/1993 | Chow | |
| 5,504,259 A | 4/1996 | Diebold et al. | |
| 5,599,510 A | 2/1997 | Kaminski et al. | |
| 5,728,271 A | 3/1998 | Piskorz et al. | |
| 5,792,340 A | 8/1998 | Freel et al. | |
| 5,865,898 A | 2/1999 | Hotzapple et al. | |
| 5,959,167 A | 9/1999 | Shabtai et al. | |
| 5,961,786 A | 10/1999 | Freel et al. | |
| 6,022,419 A | 2/2000 | Torget et al. | |
| 6,069,012 A | 5/2000 | Kayser | |
| 6,248,297 B1 | 6/2001 | Stine et al. | |
| 6,485,774 B1 | 11/2002 | Bransby | |
| 6,814,940 B1 | 11/2004 | Hiltunen et al. | |
| 6,830,597 B1 | 12/2004 | Green | |
| 6,971,594 B1 | 12/2005 | Polifka | |
| 7,044,999 B2 | 5/2006 | Bankstahl et al. | |
| 7,202,389 B1 | 4/2007 | Brem | |
| 7,262,331 B2 | 8/2007 | Van de Beld et al. | |
| 7,341,973 B2 | 3/2008 | Flego et al. | |
| 7,503,981 B2 | 3/2009 | Wyman | |
| 8,110,093 B2 * | 2/2012 | Friedman et al. ............. | 208/118 |
| 2004/0180971 A1 | 9/2004 | Inoue et al. | |
| 2005/0145542 A1 | 7/2005 | O'Connor et al. | |
| 2005/0239182 A1 | 10/2005 | Berzin | |
| 2007/0000177 A1 | 1/2007 | Hippo et al. | |
| 2007/0213573 A1 | 9/2007 | Ross et al. | |
| 2008/0009055 A1 | 1/2008 | Lewnard | |
| 2009/0011492 A1 * | 1/2009 | Berzin ....................... | 435/257.1 |
| 2009/0013601 A1 | 1/2009 | Mandich et al. | |
| 2009/0064567 A1 * | 3/2009 | Lippmeier et al. ............. | 44/308 |
| 2009/0093555 A1 | 4/2009 | Stites et al. | |
| 2009/0139851 A1 | 6/2009 | Freel | |
| 2009/0148927 A1 * | 6/2009 | Schroeder et al. ......... | 435/257.1 |
| 2009/0165378 A1 | 7/2009 | Agblevor | |
| 2009/0227823 A1 | 9/2009 | Huber et al. | |
| 2009/0294324 A1 | 12/2009 | Brandvold et al. | |

FOREIGN PATENT DOCUMENTS

| | | |
|---|---|---|
| CA | 1283880 | 5/1991 |
| CA | 2618000 A1 | 2/2007 |
| DE | 202006012176 | 12/2006 |
| EP | 1719811 A1 | 11/2006 |
| EP | 1852466 A1 | 11/2007 |
| EP | 1852490 A1 | 11/2007 |
| EP | 1852492 A1 | 11/2007 |

(Continued)

OTHER PUBLICATIONS

Lappas, A.A., et al. "Biomass Pyrolysis in a Circulating Fluid Bed Reactor for the Production of Fuels and Chemicals" Fuel IPC Science and Technology Press, Guildford, GB, vol. 81, No. 16, Nov. 1, 2002, pp. 2087-2095, XP004374414, ISSN: 0016-2361.

(Continued)

*Primary Examiner* — Jon P Weber
*Assistant Examiner* — Larry Moore
(74) *Attorney, Agent, or Firm* — Dunlap Codding, P.C.

(57) ABSTRACT

A method for producing biomass and sequestering greenhouse gas includes providing a greenhouse gas, providing light energy, and growing algae in a growth container with the greenhouse gas and the light energy. The algae can be processed into a biomass feedstock. The biomass feedstock can be converted into a fuel or specialty chemical. At least a portion of the algae can be used as a fertilizer for a biomass growth source.

9 Claims, No Drawings

(56) References Cited

FOREIGN PATENT DOCUMENTS

| | | |
|---|---|---|
| EP | 1878783 A1 | 1/2008 |
| EP | 2105486 A1 | 9/2009 |
| EP | 2107100 A1 | 10/2009 |
| WO | WO81/01713 A1 | 6/1981 |
| WO | WO02/14040 A1 | 2/2002 |
| WO | WO02/083816 A1 | 10/2002 |
| WO | WO2006/117006 A1 | 11/2006 |
| WO | WO2007/070452 A1 | 6/2007 |
| WO | WO2007/128798 A1 | 11/2007 |
| WO | WO2007/128799 A1 | 11/2007 |
| WO | WO2007/128800 A1 | 11/2007 |
| WO | WO2008/009643 A2 | 1/2008 |
| WO | WO2008/011598 A3 | 1/2008 |
| WO | WO2008/101949 A1 | 8/2008 |
| WO | WO2009/000838 A3 | 12/2008 |
| WO | WO2009/118352 A1 | 10/2009 |
| WO | WO2009/138746 A1 | 11/2009 |
| WO | WO2009/143017 A1 | 11/2009 |
| WO | WO2010/002792 A3 | 1/2010 |

OTHER PUBLICATIONS

Huber, George, W., et al. "Synthesis of Transportation Fuels From Bomass: Chemistry, Catalysts and Engineering" Chem.Rev.,; Chemical Reviews, Sep. 2006, vol. 106, No. 9, pp. 40-44-4098, 4047-4048, 4061-4063, 4085, 4092-4093, XP002490759.

McKendry, P., "Energy Production From Biomass," Bioresource Technology 83 (2002) p. 37-46.

Wyman, et al, "Coordinated Development of Leading Biomass Pretreatment Technologies" Bioresource Technology 96 (2005) 1959-1966.

Bridgwater, A.V. "Principles and Practice of Biomass Fast Pyrolysis Processes for Liquids" Journal of Analytical and Applied Pyrolysis, Jul. 1999 vol. 51, pp. 3-22, p. 15, para 4 to p. 16 para 2; p. 18, para 2.

Bridgwater, A.V., et al, "Fast Pyrolysis Processes for Biomass," Renewable and Sustainable Energy Reviews 4 (2000) 1-73.

\* cited by examiner

GROWING AQUATIC BIOMASS, AND PRODUCING BIOMASS FEEDSTOCK AND BIOCRUDE THEREFROM

FIELD OF THE INVENTION

The invention relates to growing aquatic biomass. The invention relates more particularly to growing algae, producing a biomass feedstock from the algae, and/or producing a biocrude from the biomass feedstock.

BACKGROUND OF THE INVENTION

Biomass, in particular biomass of plant origin, is recognized as an abundant potential source of fuels and specialty chemicals. See, for example, "Energy Production from Biomass" by P. McKendry, Bioresource Technology, vol. 83 (2002), pp. 37-46 and "Coordinated Development of Leading Biomass Pretreatment Technologies" by Wyman et al., Bioresource Technology, vol. 96 (2005), pp. 1959-1966. Refined biomass feedstock, such as vegetable oils, starches, and sugars, can be substantially converted to liquid fuels including biodiesel (e.g., methyl or ethyl esters of fatty acids) and ethanol. However, using refined biomass feedstock for fuels and specialty chemicals can divert food sources from animal and human consumption, raising financial and ethical issues.

Alternatively, inedible biomass or biomass grown on media that cannot support the growth of foodstuff (e.g., salt water, waste water) can be used to produce liquid fuels and specialty chemicals. For example, aquacultural biomass (e.g., micro and/or macro algae, which can grow in salt water and/or waste water) are potential feedstocks for producing fuels and specialty chemicals. Accordingly, aquacultural biomass can supplement and/or replace other source of inedible biomass such as agricultural waste (such as bagasse, straw, corn stover, corn husks, and the like), specifically grown energy crops (like switch grass and saw grass), and other sources such as trees, forestry waste (e.g., wood chips and saw dust from logging operations), paper waste, or paper mill waste.

Algae can be grown or cultivated commercially for food, vegetable oils, and other industrial products (e.g., agar). However, not all algae presently have commercial value. Algae include micro algae and macro algae. Micro algae are microscopic photosynthetic organisms, and include over 20,000 species of unicellular organisms that exist individually or in groups. Depending on the species, micro algae size can range from micrometers to hundreds of micrometers. Some micro algae can produce significant amounts of natural oils (e.g., triglycerides), which can be processed into biofuel (e.g., fatty acid alcohol esters) and unsaturated fatty acids (e.g., omega-3 fatty acids). Macro algae, more commonly known as seaweed, can grow to considerable size (e.g., 10-100 m). Macro algae are macroscopic, multicellular algae and include some members of the red, brown, and green algaes. Macro algae can be cultivated as a food source, as well as for the extraction of gelatinous substances such as alginate, agar, and carrageenan.

Oil from algae can be converted into a bio-fuel. For example, conversion of algae biomass can proceed through separation of oil from cellulosic components and conversion of the oil into a fuel such as biodiesel. Separation can reduce product yield because oil can be lost to the cellulosic component. Separation can reduce product yield because the cellulosic component must be discarded (e.g., only a fraction of the biomass is converted) or separately converted (e.g., conventional methods generally require different conditions for converting triglycerides and cellulosic component).

BRIEF SUMMARY OF THE INVENTION

The invention provides for high yielding and efficient methods and apparatuses for growing and converting algae biomass into fuels and specialty chemicals. In various embodiments, the invention includes methods, apparatuses, kits, and compositions for producing biomass and sequestering greenhouse gas. Producing biomass can include providing a greenhouse gas, providing light energy, and growing algae in a growth container with the greenhouse gas and the light energy. The algae can be processed into a biomass feedstock. The biomass feedstock can be converted into a fuel or specialty chemical through, for example, pyrolysis or catalytic cracking. At least a portion of the algae can be used as a fertilizer for a biomass growth source. Waste $CO_2$, nitrous oxides, sewage water, and waste heat from a nearby industrial facility can be recycled and used to grow algae. Thus the invention is useful for improving environmental conditions and providing environment-friendly fuels and specialty chemicals.

In one aspect, the invention features a method for producing biocrude from algae. The method includes providing algae and catalytically cracking substantially all of the organic components of the algae, to produce a biocrude.

In another aspect, the invention features a biocrude production unit. The unit includes an industrial facility providing at least one of a greenhouse gas, waste water, and waste heat to an algae growth facility. The algae growth facility employs at least one of the greenhouse gas, waste water, and waste heat to facilitate algae growth. The unit also includes a biomass catalytic cracking facility receiving algae from the algae growth facility and catalytically cracking substantially all of the algae, to produce a biocrude.

In one aspect, the invention features a method for producing biomass and sequestering greenhouse gas. The method includes providing a greenhouse gas, providing light energy, and growing algae in a growth container with the greenhouse gas and the light energy.

In other examples, any of the aspects above, or any method, apparatus, kit, or composition of matter described herein, can include anyone or more of the following features.

In various embodiments, the greenhouse gas includes $CO_2$ from an adjacent commercial or industrial facility. The $CO_2$ can be a product of converting biomass into a fuel or specialty chemical.

In some embodiments, the light energy is derived from a renewable energy source. The renewable energy can include solar energy. The light energy can be matched to the absorption spectrum of the algae. A fraction of the light energy can be used to purify the greenhouse gas. A fraction of the light energy can be used to heat the algae in the growth container.

In certain embodiments, the algae is, or includes, micro algae. The method can include providing a growth medium including fresh water.

In various embodiments, the algae is, or includes, macro algae. The method can include providing a growth medium including salt water.

In some embodiments, the growth container includes a stirring reactor with an internal light source and reflective inner wall. The growth container can include a sluice through which a suspension of the algae is circulated. The sluice can include an optically transparent region through which the light energy is provided to the algae. The suspension of the algae can include about 5% by weight micro algae in an aqueous liquid.

In certain embodiments, the growth container includes a first region allowing light energy to reach the algae and a second region preventing light energy from reaching the algae. The method can include circulating the algae between the first region and the second region and harvesting a mature fraction of the algae from the second region.

In various embodiments, the growth container includes a flexible pouch adapted for growing macro algae. The growth container can include a plastic bag adapted for growing macro algae.

In some embodiments, producing biomass includes operating the growth container at a predetermined temperature, to facilitate algae growth. The method can include providing waste heat from an adjacent commercial or industrial facility to the growth container, to facilitate algae growth.

In certain embodiments, producing biomass includes providing waste water from an adjacent commercial or industrial facility to the growth container and bio-remediating the waste water by growing algae in the waste water.

In various embodiments, producing biomass includes separating a fraction of the algae suitable for use as a fertilizer or specialty chemical. The fraction of the algae can include a mineral solution. The separating can include providing the fraction to a biomass growth source as a fertilizer.

In some embodiments, producing biomass includes providing a fertilizer to the growth container, to facilitate algae growth.

In certain embodiments, the method includes obtaining carbon credits for sequestering the greenhouse gas. The method can include purifying the greenhouse gas.

In various embodiments, growing algae includes maximizing the yield of algae mass per unit volume per unit time. The method can preferentially produce a cellulosic component relative to an oil component.

In some embodiments, producing biomass includes processing the algae into a plurality of solid biomass particles suitable for use in a biomass feedstock. The plurality of solid biomass particles can include lignocellulose. The processing can exclude an oil extraction from the algae. The processing can include de-watering the algae, agitating the algae to produce a plurality of solid biomass particles, and contacting the plurality of solid biomass particles with a catalyst. The processing can also include de-mineralizing the algae, to mitigate at least one of char and ash formation upon conversion of the biomass into a fuel or specialty chemical.

In certain embodiments, the processing includes flocculating the algae. The algae can, be flocculated with a plurality of solid catalyst particles. The plurality of solid catalyst particles can include acid alum and sodium silicate. The algae can be flocculated with a plurality of solid biomass particles. The algae can also be flocculated with immature algae cells.

In various embodiments, the plurality of solid biomass particles are torrefied biomass particles. The method can include torrefying the algae at a temperature below about 300° C., to produce a plurality of solid biomass particles having an increased brittleness and/or susceptibility to catalytic conversion.

In some embodiments, the plurality of solid biomass particles are characterized by average particle sizes of about 10 and about 2000 microns. The plurality of solid biomass particles can be characterized by average particle sizes of greater than about 1000 microns. The plurality of solid biomass particles can be characterized by average particle sizes of less than about 1000 microns. The catalyst can include a basic catalyst. Contacting the plurality of solid biomass particles with a catalyst can form a mechano-chemical interaction between the plurality of solid biomass particles and the catalyst.

In certain embodiments, producing biomass includes catalytically cracking the plurality of solid biomass particles, to produce a biocrude. The method can include providing at least a fraction of char from the catalytic cracking to the growth container as a fertilizer for growing algae. The method can also include providing char comprising carbon from the catalytic cracking to a biomass growth source, to fertilize the biomass growth source.

In various embodiments, the biocrude is characterized by a total acid number of less than about 20 and can be converted into a fuel or specialty chemical using a conventional petrochemical processing or refining unit. The biocrude can be characterized by a strong acid number of less than about 5. The biocrude can be characterized by a pH value of above about 4. The biocrude can be characterized by a low corrosiveness.

In some embodiments, producing biomass includes preventing undesired biological contamination of the growth container.

In certain embodiments, producing biomass includes purifying a liquid comprising sewage by growing algae in the liquid. The purifying can include separating purified water from the liquid with a one-way osmotic membrane in fluid communication with the growth container.

In various embodiments, the method includes supplying a growth medium comprising waste water. The method can include providing the greenhouse gas at a pressure greater than atmospheric pressure. The method can include sparging a gas into the growth container. The method can include scrubbing a gas from the growth container.

In some embodiments, the method includes selecting algae that maximizes total mass grown per unit volume per unit time. The method can include excluding a separation of algae oil from algae solid. In one embodiment, the algae includes carbon provided directly from an adjacent industrial facility. The method can include providing a greenhouse gas; providing light energy; and growing algae in a growth container with the greenhouse gas and the light energy. In one embodiment, the method includes upgrading the biocrude, to produce a fuel or specialty chemical.

In certain embodiments, the industrial facility includes the biomass catalytic cracking facility.

DETAILED DESCRIPTION OF THE INVENTION

In various embodiments, the invention includes methods, apparatuses, kits, and compositions for growing algae, producing biomass feedstock from algae, and converting the biomass feedstock into fuels and/or specialty chemicals.

The invention includes a method for producing biocrude from algae. For example, a method can include providing algae (e.g., growing, collecting, purchasing algae or waste algae cake) and catalytically cracking substantially all of the organic components of the algae, to produce a biocrude. Because the method can convert substantially all of the algae mass (e.g., both lipid and carbohydrate components), algae can be selected that maximizes total mass grown per unit volume per unit time (e.g., as opposed to maximizing lipid components, for example, to produce bio-diesel). Furthermore, the algae can be effectively catalytically cracked while having essentially the same macromolecular content (e.g., proportions of lipid, carbohydrate, amino acid, and nucleic acid) as when the algae was harvested (e.g., the method can exclude a separation of algae oil from algae solid). Even more, residual algae solids can be catalytically cracked after the extraction of triglycerides used for the production of biodiesel. Therefore, the methods can reduce waste and increase total yield by facilitating the use of higher yielding algae and by converting more of the algae mass to product.

The invention also includes apparatuses for producing biocrude from algae. For example, an apparatus can include a biocrude production unit having an industrial facility, an algae growth facility, and a biomass catalytic cracking facility. The industrial facility (e.g., petroleum refinery, power plant, biomass catalytic cracking unit, or other facility that can emit a greenhouse gas) provided at least one of a greenhouse gas, waste water, and waste heat to the algae growth facility. The algae growth facility employs at least one of the greenhouse gas, waste water, and waste heat to facilitate algae growth. The biomass catalytic cracking facility receiving algae from the algae growth facility and catalytically cracking substantially all of the algae, to produce a biocrude. Therefore, the apparatuses can function synergistically to reduce undesirable waste products and environmental impact (e.g., greenhouse gas, waste water, solid waste from unconverted biomass) while increasing desirable product yield (e.g., biocrude, fuels, specialty chemicals).

Furthermore, the invention includes methods for growing algae. For example, algae can be grown by providing a greenhouse gas, providing light energy, and growing algae in a growth container with the greenhouse gas and the light energy. The algae can sequester the greenhouse gas (e.g., carbon dioxide) and produce organic compounds (e.g., oils, carbohydrates) using the light energy. The algae can also bioremediate waste water. The growth container can be designed, and growth conditions and algae type can be selected to maximize the total yield of algae solids per unit volume per unit time. Algae can be harvested and processed into a plurality of solid biomass particles suitable for use as a biomass feedstock, which can then be converted into a fuel or specialty chemical. For example, the solid biomass particles can be in contact with a catalyst and subjected to pyrolysis or catalytic cracking, to produce a biocrude.

The biocrude (e.g., from any of the methods or apparatuses of the invention) can be upgraded into a fuel or specialty chemical. Examples of fuels include light gases (e.g., ethane, propane, butane), naphtha, distillates (e.g., jet fuel, diesel, heating oil), and the like. Examples of chemicals include light olefins (e.g., ethylene, propylene, butylenes), acids (e.g., formic, acetic), aldehydes, alcohols (e.g., ethanol, propanol, butanol, phenols), ketones, furans, and the like.

Biomass

Biomass includes materials produced by photosynthetic conversion of carbon dioxide and water using light. Biomass sources include, but are not limited to, algae, grains, grasses, sugar cane, trees, and the like. Biomass sources also include by-products of agricultural or forestry activities, such as straw, chopped straw, cotton linters, corn husks, corn stalks, corn cobs, wood chips, saw dust, bagasse, sugar beet pulp, tree bark, grasses, and the like. Biomass sources also include aquatic sources such as micro algae (e.g., diatoms and green, blue-green, and golden algae) and macro algae (e.g., seaweed). Such biomass generally includes lipids (e.g., glycerides and aliphatic hydrocarbons), as well as carbohydrates (e.g., amorphous hemicellulose, and/or crystalline cellulose), lignin, polypeptides (e.g., proteins), and minerals. Some aquatic plants include little or no lignin.

Algae can be a suitable source of biomass because they can exhibit one or more of high growth rates, conversion efficiency (e.g., can convert more solar energy into biomass than many terrestrial plants), and hardiness (e.g., can grow under more adverse conditions than many terrestrial plants, such as salt water). Growing algae also do not require the use of arable land, and thus does not necessarily compete with farming conventional foodstuffs.

To produce biomass feedstock from algae, one can select algae that maximized total biomass yield per unit volume per unit time. Some algae that maximize total biomass yield can have a relatively high content of carbohydrates (e.g., cellulose, hemicelluloses) and lignin, which are not necessarily suitable for producing biofuel using conventional methods (e.g., conversion of plant oil into biodiesel). Exemplary macromolecule compositions of various algae species are provided in Table 1. In some examples, the selected algae species can preferentially produce a cellulosic component relative to an oil component. For example, algae species having relatively low lipid content but high carbohydrate content (e.g., *Spirogyra* sp., *Dunaliella salina, Porphyridium cruentum*, and *Anabaena* cylindrical) can be cultivated to produce a biomass feedstock.

TABLE 1

Chemical Composition of Algae (wt % Dry Matter)

| Strain | Protein | Carbo-hydrates | Lipids | Nucleic acid |
| --- | --- | --- | --- | --- |
| *Scenedesmus obliquus* | 50-56 | 10-17 | 12-14 | 3-6 |
| *Scenedesmus quadricauda* | 47 | — | 1.9 | — |
| *Scenedesmus dimorphus* | 8-18 | 21-52 | 16-40 | — |
| *Chlamydomonas rheinhardii* | 48 | 17 | 21 | — |
| *Chlorella vulgaris* | 51-58 | 12-17 | 14-22 | 4-5 |
| *Chlorella pyrenoidosa* | 57 | 26 | 2 | — |
| *Spirogyra* sp. | 6-20 | 33-64 | 11-21 | — |
| *Dunaliella bioculata* | 49 | 4 | 8 | — |
| *Dunaliella salina* | 57 | 32 | 6 | — |
| *Euglena gracilis* | 39-61 | 14-18 | 14-20 | — |
| *Pymnesium parvum* | 28-45 | 25-33 | 22-38 | 1-2 |
| *Tetraselmis maculata* | 52 | 15 | 3 | — |
| *Porphyridium cruentum* | 28-39 | 40-57 | 9-14 | — |
| *Spirulina platensis* | 46-63 | 8-14 | 4-9 | 2-5 |
| *Spirulina maxima* | 60-71 | 13-16 | 6-7 | 3-4.5 |
| *Synechoccus* sp. | 63 | 15 | 11 | 5 |
| *Anabaena cylindrica* | 43-56 | 25-30 | 4-7 | — |

Suitable growth conditions for growing algae can be determined to maximize the yield of algae solid per unit volume per unit time. For example, growing algae requires certain amounts of light energy, carbon dioxide, oxygen, and nutrients (e.g., phosphates, nitrates, and ammonia). Other conditions such as sufficient mixing, temperature, pH, and contamination can affect algae growth. In general, micro algae are grown in fresh water. In general, macro algae are grown in salt water (e.g., seawater, brackish water) and can require a firm attachment point.

Algae can be cultured in open systems (e.g., ponds, lakes). For example, algae can be grown in an open raceway pond. Open systems can provide a large growth space (e.g., suitable for growing large amounts of micro algae or for growing large macro algae varieties, which can grow, for example, up to 60 m or greater in length). However, open systems can be susceptible to environmental contamination by bacteria, fungi, plants, and/or animals. Open systems are also susceptible to environmental temperature and lighting conditions, and can have a growing season influenced by local climate and/or season.

Algae can be cultured in closed systems (e.g., growth containers) such as stirred-tank reactors, photobioreactors, and flowing tube bundle reactors. Nutrients and supplements (e.g., phosphates, nitrides, ammonia and minerals) can be introduced into a closed system under controlled conditions, or can be augmented to improve algae growth. Light (e.g., intensity, wavelength), gasses (e.g., $CO_2$, $O_2$), and/or growth media (e.g., quality and quantity of water) can be controlled in a closed system. Because the system is closed, contamination by other organisms such as invasive algae species, bacteria, plants, animal, and/or fungi can be mitigated. Closed systems can also allow control for environmental conditions, facilitating year-round or extended growth time (e.g., more hours per day, days per year).

Harvesting Biomass

Algae can be harvested at any point in its growth cycle by removing the algae from the growth medium. For example, algae can be harvested at maturity (e.g., at or about the plateau on the growth curve, at or about a certain cell or organism size). Algae can be harvested to achieve a desired yield of total biomass per unit volume per unit time. However, algae can be harvested at an earlier or later time to meet a production need.

In some embodiments, the growth system can operate in a continuous mode and only a fraction of the algae will be harvested at one time. For example, mature algae can be substantially separated from immature algae, the mature algae harvested, and the immature algae allowed to continue growing. Because mature and immature algae vary in their physical properties (e.g., density), they can be separated. For example, mature algae can aggregate at a first height in a tank (e.g., a dark tank in a closed, circulating system) and immature algae can aggregate at a second height. Alternatively, mature algae can be separated from immature algae by screening, filtering, centrifuging, and the like. Immature algae can be allowed to continue growing. In some embodiments, the growth system can operate in a batch mode and all of the algae will be harvested at one time. In some cases mature algae can provide higher amounts of biomass per unit volume than immature algae.

Algae can be harvested as a slurry of aquatic biomass. The slurry can be obtained by collecting the algae (e.g., through centrifugation, froth floatation, flocculation) and dewatering the algae (e.g., passing the algae over a screen and allowing water to drain by the action of gravity). A slurry can include about 10 to about 35 wt % water, although higher and lower wt % of water are possible (e.g., to control flow properties or prepare the slurry for further processing). Water can be removed from harvested algae or a slurry by mechanical action or other physical action (e.g., cyclonic or centrifugal force). For example, water can be removed in disintegrating (e.g., mechanical size reduction), agitating, and/or kneading steps. Water can be removed by screening or filtering (e.g., gravity or press filtering). In some examples, water can be removed using passive (e.g., drying in the sun) or active (e.g., heating) evaporation.

Harvesting can include flocculating algae. Algae can be difficult to disintegrate because they are flexible and thus can resist being cut or broken apart. Flocculation can combine individual algae cells or tissue into a structure that can be more readily disintegrated. Flocculation can also form a particle that can be used directly as a solid biomass particle (e.g., not require particle size reduction prior to pre-processing or processing). Algae can self-flocculate and/or can flocculate onto particles of another substance. Flocculated algae (with or without other particles or catalyst) can be subjected to a pre-processing step or proceed directly to a processing step.

Algae can be flocculated with a plurality of solid catalyst particles. In one example, a mixture of acid alum and/or sodium silicate can be with algae, to flocculate the algae. Flocculating the mixture with the algae can be facilitated by an acidic pH (e.g., lower than 7).

Algae can be flocculated with a plurality of solid biomass particles. For example, algae can be contacted (e.g., filtered through a bed or slurry) with biomass particles and at least a portion of the algae can be deposited on a surface of the biomass particles. The deposited algae can then be dried and/or torrefied on the surface of the biomass particles. The biomass particles can be torrefied biomass particles, or biomass particles pre-treated to decrease hydrophobicity.

Algae can be flocculated with char or a solid byproduct of pyrolysis or catalytic cracking. Immature algae can be used as a flocculent.

Pre-Treating Biomass

In various embodiments, biomass feedstock can be chemically and/or physically pre-treated. Examples of pretreatment steps in which recycled aqueous phase can be used include demineralization, heat treatment, and steam explosion.

Demineralization can include removing at least a fraction of a naturally occurring mineral from biomass (e.g., prior to a pyrolysis or catalytic cracking reaction). Demineralization can improve control over the reaction of the biomass. Many of the minerals naturally present in the biomass material can be catalytically active (e.g., potassium, iron). Although these materials can catalyze reactions, they can also increase coke yield, which is generally undesirable. Even when catalytic activity is desired, it can be preferable to first demineralize the biomass material so as to control the composition of their catalyst system.

One method of demineralization includes contacting biomass with an aqueous solvent and allowing the biomass material to swell. After swelling, at least part of the aqueous solvent can then be removed from the biomass by mechanical action (e.g., kneading, pressing). Swelling and dewatering steps can be repeated to control the amount of minerals that are removed from the biomass. In addition to removing minerals from the biomass, the swelling and dewatering steps can make the biomass material more susceptible to a subsequent reaction.

Although essentially any aqueous solvent can be used for demineralization, the aqueous phase of a liquid pyrolysis product can be particularly effective. The effectiveness is believed to be due to the presence of organic acids (e.g., carboxylic acid, acetic acid) in the aqueous phase. Without wishing to be bound by any theory, the acidity of the aqueous phase can facilitate the mobilization of minerals in the biomass. For example, the chelating effects of carboxylic acids can contribute to the solubilization and removal of mineral cations.

De-mineralizing biomass (e.g., algae) can mitigate at least one of char and ash formation upon conversion (e.g., pyrolysis, catalytic cracking) of the biomass into a fuel or specialty chemical by removing the mineral precursors of the char and/or ash from the biomass. De-mineralizing biomass (e.g., algae) can also produce a fertilizer by separating a fraction of the biomass suitable for use as a fertilizer or specialty chemical. The fraction of the biomass can include a mineral solution as a raw extract (e.g., essentially the solvent removed during demineralization) or as a fraction of the raw extract (e.g., water, mineral, or other component at least partially removed).

Solvent explosion can include contacting the biomass with a pressurized solvent at a temperature above its natural boiling point (e.g., at atmospheric pressure). The pressurized solvent is in a liquid phase and swells the biomass. Then, the solvent is de-pressurized, causing rapid evaporation (e.g., boiling) of the solvent. This rapid evaporation can be referred to as solvent explosion. The solvent explosion can physically rupture the biomass material, thereby making it more accessible in a subsequent reaction.

Examples of solvents that can be used in solvent explosion include ammonia, carbon dioxide, water, and the like. If water is used as the solvent, the process can be referred to as steam explosion. It is understood that the term steam explosion can be considered a misnomer, and that the term water explosion can be more accurate. Nevertheless, the term steam explosion is used herein because it is an accepted term of art. The aqueous phase of the liquid pyrolysis product can be used in a steam explosion.

When steam explosion is combined with demineralization, the steam explosion can be carried out before or after the demineralization. For example, it can be advantageous to conduct the demineralization after the steam explosion because the steam explosion pretreatment can make the minerals more accessible, thereby making the demineralization more effective.

Heat treatment (e.g., torrefaction) can include heating the biomass to a temperature of about 100-300° C. in an oxygen-poor or oxygen-free atmosphere. The term oxygen-poor can refer to an atmosphere containing less oxygen than ambient air. The heat treatment can carried out in the presence of sufficient solvent (e.g., water) to swell the biomass material. The heat treatment can be carried out in a closed vessel to mitigate evaporation of the solvent. In some examples, the vapor (e.g., steam) formed under these conditions can displace oxygen present in the vessel and produce an oxygen-poor atmosphere. In one example, the aqueous phase of a liquid pyrolysis product can be the solvent in such a heat treatment.

Heat treatment can be carried out at a temperature low enough to mitigate carbon loss due to the formation of gaseous conversion products (e.g., CO, $CO_2$). A heat treatment can use, for example, a temperature of about 100-200° C. For example, a temperature can be about 100-140° C. A heat treatment can have a duration, for example, of about 2 min to 2 hours. For example, a duration can be about 20-60 min. In various examples, pressure can be released at the end of a heat treatment by opening the heat treatment vessel, which can allow the heat treatment to be combined with a steam explosion pretreatment step.

Even when the heat treatment essentially does not produce any gaseous conversion products, it can still result in a modification of the biomass. For example, the heat treatment can make the biomass more brittle and more hydrophobic. Both effects can be desirable from the perspective of a subsequent reaction. For example, increased brittleness can facilitate girding the biomass to a small particle size, to increase reactivity in a pyrolysis reaction, and increased hydrophobicity can facilitate drying the biomass.

In one embodiment, a method of producing a biomass feedstock from algae can include torrefying the algae at a temperature below about 300° C., to produce a plurality of solid biomass particles having an increased brittleness and/or susceptibility to catalytic conversion.

A heat pretreatment step can be combined with one or more additions pretreatment steps (e.g., demineralization, steam explosion). Because of the increased hydrophobicity of heat treated biomass, it can be preferable to conduct any demineralization and/or steam explosion steps prior to the heat treatment; with the exception that steam explosion can be combined with heat treatment as described above.

Disintegrators, Agitators, and Kneaders

A disintegrator processes plant matter, to produce solid biomass particles. In operation, a disintegrator can be used to modify the consistency of, e.g., biomass feedstock, and/or to reduce its average particle size. The disintegrator can include at least one of a mill, fragmenter, fractionator, granulator, pulverizer, chipper, chopper, grinder, shredder, mincer, and a crusher. Apparatuses including a disintegrator can process plant matter at a location in close proximity to an agricultural site used to produce such plant matter (e.g., algae growth facility), to produce the solid biomass particles. U.S. Pat. No. 6,485,774 to Bransby, the disclosure of which is incorporated herein by reference in its entirety, discloses a method of preparing and handling chopped plant materials. In particular, the text corresponding to column 1, line 45 to column 4, line 65 of U.S. Pat. No. 6,485,774 is incorporated herein by reference.

In various embodiments, the method includes agitating solid biomass particles, to reduce a size characterizing at least a portion of the particles. Agitation can be carried out by various different methods and in various different vessels. For example, in order of increasing abrasion, the agitation can be carried out in a fluid bed, a bubbling or ebullient bed, a spouting bed, or a conveyor. In one embodiment, agitation is carried out by fluid conveyance, including without limitation, by gas flow or pneumatic conveyance. In one embodiment, agitation is carried out in a riser or a downer.

In various embodiments, agitating solid biomass particles, to reduce a size characterizing at least a portion of the particles, is facilitated by agitating solid biomass particles together with a material that is harder than the biomass. For example, the material can be a catalyst or another inorganic particulate material. In embodiments using an abrading or grinding material that is a catalyst, the catalyst can become embedded in the biomass particles, which can facilitate catalytic conversion of the biomass. In such embodiments, agitating can facilitate formation of a mechano-chemical interaction between at least a portion of the catalyst and at least a portion of the solid biomass particles, which can facilitate catalytic conversion of the biomass.

Agitation can be carried out at an elevated temperature, for drying the biomass. An elevated temperature can be a temperature sufficient to dry the biomass, for example, between about 50 and about 150° C., below about 200° C., or below about 300° C. Higher temperatures can be used, for example, where an agitating gas is oxygen-poor or substantially oxygen-free. Agitation can also be carried out at ambient temperature with dried biomass. Drying increases the hardness of the biomass particles, making the particles more susceptible to size reduction.

International Publication No. WO 2007/128798 A1 by O'Connor, the disclosure of which is incorporated herein by reference in its entirety, discloses agitating solid biomass particles and catalysts. In particular, paragraphs [0027] to [0072] of WO 2007/128798 A1 are incorporated herein by reference.

International Publication No. WO 2008/009643 A2 by O'Connor, the disclosure of which is incorporated herein by reference in its entirety, discloses agitating solid biomass particles and catalysts. In particular, paragraphs [0009] to [0051] of WO 2008/009643 A2 are incorporated herein by reference.

A kneader can be used to knead the solid biomass particles and the catalyst, to make at least a portion of the solid biomass particles accessible to at least a portion of the catalyst. The kneader can be an extruder, miller, mixer, or grinder. The kneader can operate at greater than ambient temperature, for example, to facilitate removal of water and/or other solvent. For example, the kneader can be heated and/or heated gas (e.g., steam) can be provided to heat the biomass and catalyst. In various embodiments, the kneader employs a solvent. The solvent can be water, an alcohol (e.g., ethanol or glycerol), a bio-oil or another product from the conversion of the biomass, a liquid acid, an aqueous solution of an acid or base, liquid $CO2$, and the like. In various embodiments, the biomass can be kneaded with one or more solid catalyst and/or inorganic particulate material.

Any one or more of disintegrating, agitating, and kneading the biomass can be conducted before, during, and/or after pre-treating the biomass. Similarly, contacting biomass with a catalyst can be conducted before, during, and/or after disintegrating, agitating, kneading, and pre-treating the biomass. Contacting biomass with a catalyst can result in a simple mixture, or can result in one or more of a mechanical, physical, and chemical interaction between the biomass and catalyst.

In various examples, a method can include processing algae into a plurality of solid biomass particles suitable for use in a biomass feedstock. In one example, the method can include: de-watering the algae, produce a plurality of solid biomass particles from the dewatered algae, and contacting the plurality of solid biomass particles with a catalyst. The process of producing a biomass feedstock can exclude an oil extraction from the algae where the feedstock is not limited to a plant oil based feedstock.

Solid Biomass Particles

In various embodiments, biomass feedstock can include particles that are solid and in a finely divided form (e.g., saw dust and ground straw). Biomass feedstock can include solid materials as well as materials that might be classified as liquids, but that have a very high viscosity (e.g., small or large colony algae). Biomass particles can be prepared from biomass sources and larger particles by techniques such as milling, grinding, pulverization, and the like.

The biomass can be subjected to a particle size reduction step, or can be collected in the form of particles (e.g., algae cells, colonies, flocculated algae, and the like). In various embodiments, the biomass particles are reduced to, or have, an average particle size of less than about 1000 microns. Alternatively, the biomass particles are reduced to, or have, an average particle size of greater than about 1000 microns. In general, at least a fraction of the biomass particles have a size of about 1-2000, 1-1000, or 1000-2000 microns. For example, the biomass particles can have an average size of less than about 2000, 1750, 1500, 1250, 1000, 750, 500, or 250 microns. In some embodiments, at least a fraction of the biomass particles are reduced to a size below about 500, 475, 450, 425, 400, 375, 350, 325, 300, 275, 250, 225, 200, 175, 150, 125, 100, 90, 80, 70, 60, 50, 40, 30, 20, 15, 10, or 5 microns. Individual particles sizes can range from microns, to tens of microns, to tenths of centimeters, to centimeters or greater.

Solid biomass particles do not necessarily assume a spherical or spheroid shape. For example, solid biomass particles can be needle shaped and/or assume another cylinder-like or elongated shape. Accordingly, size does not necessarily correspond to a single diameter (although it could correspond to an average diameter or diameter in a single, for example largest or smallest, dimension). In various embodiments, size can correspond to the mesh size or a screen size used in separation and/or sizing the solid biomass particles.

Biomass Conversion

Converting a biomass feedstock into a biocrude can include techniques from biomass and/or petroleum processing. Biomass can be converted, for example, by thermal processes such as pyrolysis. Pyrolysis is, in general, the chemical decomposition of a solid substance (e.g., biomass) by heating the solid substance. Biomass can also be converted into a fuel or a specialty chemical by catalytic cracking (e.g., biomass catalytic cracking (BCC), as well as other fluid catalytic cracking (FCC) type processes adapted from conventional petrochemical processing). Catalytic cracking can de-oxygenate, and thus liquefy, biomass to produce a liquid product. For example, catalytically cracking a plurality of solid biomass (e.g., from algae) can produce a biocrude. A fraction (e.g., a bio-oil) can be separated from the biocrude. The fraction can be a final product, or can be subjected to further refining and/or processing to produce a final product.

A catalyst can be any material that facilitates the conversion of organic components of the biomass into fuels, specialty chemicals, or precursors thereof. In various embodiments, the catalyst includes a solid particulate catalyst and at least a portion of the catalyst interacts mechano-chemically with at least a portion of the solid biomass particles. The particulate inorganic oxide can be a refractory oxide, clay, hydrotalcite, crystalline alumino silicate, layered hydroxyl salt, or a mixture thereof. Other suitable catalysts include lime, brine, and/or bauxite dissolved in a base (e.g., NaOH), or a natural clay dissolved in an acid or a base, or fine powder cement (e.g., from a kiln). In some embodiments, a catalyst can be a catalytic metal used alone or together with another catalyst. In certain embodiments, the catalyst includes a basic catalyst.

In various embodiments, a catalyst is a particulate inorganic oxide. The particulate inorganic oxide can be a refractory oxide, clay, hydrotalcite, crystalline alumino silicate, layered hydroxyl salt, or a mixture thereof. Suitable refractory inorganic oxides include alumina, silica, silica-alumina, titania, zirconia, and the like. Suitable clay materials include cationic and anionic clays, for example, smectite, bentonite, sepiolite, atapulgite, hydrotalcite, and the like. Suitable metal hydroxides and metal oxides include bauxite, gibbsite and their transition forms. Other suitable (and inexpensive) catalysts include lime, brine, and/or bauxite dissolved in a base (e.g., NaOH), or a natural clay dissolved in an acid or a base, or fine powder cement (e.g., from a kiln). Suitable hydrotalcites include hydrotalcite, mixed metal oxides and hydroxides having a hydrotalcite-like structure, and metal hydroxyl salts.

In some embodiments, a catalyst can be a catalytic metal. The catalytic metal can be used alone or together with another catalyst. A catalytic metal can be used in a metallic, oxide, hydroxide, hydroxyl oxide, or salt form, or as a metalloorganic compound, or as a material including a rare earth metal (e.g., bastnesite). In certain embodiments, the catalytic metal is a transition metal. The catalytic metal can be a non-noble transition metal. For example, the catalytic metal can be iron, zinc, copper, nickel, and manganese. In one embodiment, the catalytic metal is iron.

Contacting the catalyst with the biomass can be achieved by various methods. One method includes heating and fluidizing a mixture of the particulate biomass material, and adding the catalyst to the mixture as fine solid particles. Another method includes dispersing the catalytic material in a solvent (e.g., water), and adding the solvent to the mixture of particulate biomass material.

In various embodiments, the biocrude is characterized by a total acid number (TAN) of less than about 20. TAN includes strong acids (e.g., carboxyl acids) and weak acids (e.g., phenols), so it does not necessarily correlate directly with pH. The total acid number of the biocrude can be between about 15 and about 20, between about 10 and about 15, between about 5 and about 10, or less than about 5, 4, 3, 2, or 1. One advantage to a biocrude that is characterized by a total acid number of less than about 20, is that it can be converted into a fuel or specialty chemical using a conventional petrochemical processing or refining unit.

In certain embodiments, the biocrude has a strong acid number of less than about 5. For example, the strong acid number of the biocrude can be between about 4 and about 5, between about 3 and about 4, between about 2 and about 3, between about 1 and about 2, or below about 1. In some embodiments, the biocrude has a pH value of above about 4. For example, the pH of the biocrude can be between about 4 and about 4.5, between about 4.5 and about 5, between about 5 and about 5.5, between about 5.5 and about 6, between about 6.5 and about 7, or above about 7.

Biocrude can be characterized by a low corrosiveness (e.g., low total acid number, low strong acid number, neutral to mildly acidic pH, and the like). Low corrosiveness can prevent or mitigate damage to production, refining, transportation, and/or storage equipment.

Through processing and refining, the biocrude can be converted into a fuel or specialty chemical. In various embodiments, the biocrude includes hydrocarbons from which oxygen is stripped (e.g., as $CO$, $CO_2$, $H_2O$) to produce traditional fuel or specialty chemical products. In general, processing proceeds by cracking and deoxygenating (as necessary) polymeric compounds in the biomass and biocrude. Examples of fuels include light gases (ethane, propane, butane), naphtha, distillates, jet fuel, diesel, heating oil), and the like. Examples of chemicals include light olefins (ethylene, propylene, butylenes), acids (like formic and acetic), aldehydes, alcohols (ethanol, propanol, butanol, phenols), ketones, furans, and the like.

Catalytic cracking can also produce char and/or ash as a by-product, at least a fraction of which can include phosphorous and nitrogen in a chemical form useful as a fertilizer. The fraction of char and/or ash can be provided to the growth container as a fertilizer for growing algae. More generally, the fraction of char and/or ash can be provided to a biomass growth source as a fertilizer (e.g., for growing crops).

Bioremediation

In various embodiments, the method includes sequestering a greenhouse gas. For example, at least a fraction of the greenhouse gas used in growing algae can be provided by an adjacent to a commercial or industrial facility (e.g., a coal or waste burning power plant, petroleum refinery unit, biomass catalytic cracking unit, and the like). The algae can fix the carbon dioxide into biomass using photosynthesis. In some cases, the algae can sequester another greenhouse gas (e.g., CO, nitrous oxides, and the like) by absorbing and/or metabolizing the gas.

Furthermore, the method includes obtaining carbon credits by sequestering a greenhouse gas. For example, the method can include measuring the amount of greenhouse gas sequestered by the algae and obtaining, or trading the right to obtain, carbon credits from an agency (e.g., private or local, state, or federal government).

In various embodiments, the method includes purifying waste water. In one example, the method includes providing waste water from an adjacent commercial or industrial facility to the growth container and bio-remediating the waste water by growing algae in the waste water. In one example, the method includes purifying a liquid comprising sewage by growing algae in the liquid and, optionally, separating purified water from the liquid with a one way osmotic membrane in fluid communication with the growth container.

Purifying waste water can include any one or more of removing organic solids, organic compounds (e.g., hydrocarbons, solvents, and other industrial reagents or waste products), competitive biological species (bacterium, unfavorable algae, fungi, etc.), inorganic compounds (e.g., phosphate, nitrates, ammonia, and the like, which can also act as fertilizer for the algae), minerals, and/or metals from the water. Where a substance removed from the waste water is toxic or undesirable, it can be removed in the process of producing a biomass feedstock.

Examples

In various embodiments, the invention provides a method for producing biomass and sequestering greenhouse gas. The method includes providing a greenhouse gas, providing light energy, and growing algae in a growth container with the greenhouse gas and the light energy. The algae can include one or more strains of micro and/or macro algae.

The greenhouse gas can include $CO_2$. The $CO_2$ can be from one or more of a gas source, the atmosphere, and a commercial or industrial facility. For example, the $CO_2$ can be from an adjacent coal-fired electric plant, trash incinerator, petroleum refinery, or biomass conversion unit. The $CO_2$ can be a product of converting biomass into a fuel or specialty chemical. The $CO_2$ content, or other gas content, of the greenhouse gas can be controlled by purifying, refining, and/or supplementing the greenhouse gas. Purification of the greenhouse gas can also be used to remove undesirable components (e.g., toxic chemical substances and/or biological contaminants) from the greenhouse gas.

The light energy can be provided by the sun or a lamp. A lamp can be powered by renewable energy sources such as solar, wind, hydroelectric, tidal, geothermal, and the like. The light energy (e.g., from a lamp) can be selected to match the absorption spectrum of the algae. For example, red light (e.g., about 620-750 nm wavelength) can be preferred by many algae species.

The light energy can be used to directly heat the algae in the growth container, to maintain a desired temperature. Electric energy can also be generated from the light energy or another energy source, to heat the algae in the growth container. Alternatively, the algae in the growth container can be heated by another method such as hydrocarbon combustion. However actively heating the algae in the growth container is not required. For example, light energy provided for growing the algae can also passively heat the algae. Light energy can be used to purify the greenhouse gas. For example, the UV fraction of the light can be used to neutralize biological contaminants and/or sterilize the greenhouse gas.

The light energy can be provided continuously or intermittently. While light energy is required for algae to grow, portions of algae metabolism do not require light (e.g., respiration). Algae growth can benefit from a period where light energy is not provided. Absorption of light energy beyond the algae's photosynthetic capacity can damage the algae (e.g., free radicals) and cause photoinhibition. Therefore, the light energy can be provided for a fixed or varying duration of up to 24 hours. For example, a period can be about 1, 2, 3, 4, 5, 6, 7, 8, 9, 10, 11, 12, 13, 14, 15, 16, 17, 18, 19, 20, 21, 22, 23, and up to 24 hours per day. Note that periods of light and dark can be controlled such that a day-like cycle is effectively more or less than 24 hours. The light energy can be controlled by turning a light source on or off, or by blocking the light (e.g., by a shade, circulating algae into a dark tank). In some examples, the light energy can be provided as pulsed radiation. For example, the pulsing can be at a high frequency (e.g., at or about a typical AC current). In some examples, the light energy can be switched between wavelengths.

Algae can be grown in a growth container with the greenhouse gas and the light energy. The growth container can contain a growth medium for the algae (e.g., fresh water, salt water, or other aqueous medium). The growth container can include one or more vessels containing the algae and growth medium. A vessel can be flexible (e.g., flexible pouch or sluice, plastic bag) or inflexible (e.g., plastic or metal tank, pipe), and can have a feature for accomplishing a specific function (e.g., transmitting or blocking light energy). The growth container can include ports for receiving or releasing light energy, growth medium, gas, supplements, algae, and the like. The growth container can also include one or more pumps, mixers, impellers, and/or stirrers to circulate and/or mix the algae. The growth container can also include one or more environmental control systems, for example, to measure and/or control temperature, light energy, gas concentration, nutrient concentration, toxin concentration, and/or algae growth.

Examples of growth containers include continuous stirred-tank reactors (CSTR), photobioreactors, and flowing tube bundle reactors. In a CSTR, one or more fluids can be introduced into a tank reactor equipped with an impeller. The impeller stirs the fluids to ensure proper mixing. A photobioreactor is a closed system that incorporates a light source and is used to grow phototrophic small organisms such like micro algae. A flowing tube bundle reactor is like a vertical shell and tube heat exchanger consisting of a shell with a bundle of tubes inside. One fluid (e.g., algae and growth medium) runs through the tubes, and another fluid (e.g., water, for example, at 30-35 0 C) flows over the tubes (through the shell) to transfer heat between the two fluids. In some embodiments, the growth container includes a flexible pouch and/or a plastic bag adapted for growing macro algae, to provide sufficient space for macro algae growth.

In one example, the growth container includes a stirring reactor with an internal light source and a reflective inner wall. The stirrer that mixing of the growth medium, to provide a uniform distribution of dissolved gasses and nutrients in the growth medium. The internal light source can be an artificial light source (e.g., fiber optics centralized on the stirrer, LED arrays) and can supplement or supplant light from outside the growth container. The reflective inner wall can be a highly polished or mirrored surface, which increases the amount of the light energy that reaches the algae.

In another example, the growth container includes a sluice through which a suspension of the algae is circulated. For example, the growth container can include a sluice or other vessel through which a 5% by weight aqueous suspension of micro algae is circulated. The sluice includes an optically transparent region through which the light energy is provided to the algae.

For example, the growth container can include a first region allowing light energy to reach the algae (e.g., a transparent or translucent region or window) and a second region preventing light energy from reaching the algae (e.g., an opaque or dark region, conduit, or tank). In such a growth container, one can circulate the algae between the first region and the second region and harvest a mature fraction of the algae from the second region. Algae can be contained in the second region for a predetermined period (e.g., about 4 hours of 24 hours). After the mature fraction is harvested, the remaining algae can continue to circulate and grow.

The growth medium can include an aqueous solution of nutrients (e.g., fertilizer) and salts, as appropriate. Nutrients such as phosphates, nitrates, and ammonia can be added to the growth container. In some embodiments, the nutrients are byproducts of biomass processing and/or conversion. For example, phosphates and nitrates can be collected from char and/or ash produced during biomass catalytic cracking. Ammonia can be collected from a catalytic cracking reactor unit.

Growth conditions such as temperature and pH can be controlled in the growth container. In some embodiments, the growth container operates at a predetermined temperature to facilitate algae growth (e.g., about 15-30° C.). The temperature can be maintained by providing heat energy to the growth container (e.g., from the light energy, waste heat from an adjacent commercial or industrial facility, and/or a conventional heat source such as an electric or hydrocarbon fuel heater). In various algae, the growth temperature can modulate the macromolecular composition (e.g., % lipid, carbohydrate, protein) in addition to the growth rate. A predetermined pH value of the growth medium can also be monitored and maintained to facilitate algae growth. For example, some algae grow faster in alkaline medium. An alkaline pH can also increase the solubility of $CO_2$ in water.

Biological contamination in the growth container and/or growth facility can be prevented. For example, the growth container can include a system for preventing viruses, bacteria, fungi, plants (including undesired algae), insects, and/or animals from entering the growth container. The system can be a passive system such as sealing the container and/or a unit housing the container, to prevent undesired entry. The system can include one or more filters, to prevent entry with gases, fluids, and/or solids entering the growth container. The system can also include sterilization equipment, to sterilize gases, fluids, and/or solids entering the growth container (e.g., using radiation, such as UV radiation from the light energy source, to destroy biological contaminants). In various embodiments, the system can include one or more of using ethylene, propylene, or n-hexane during $CO_2$ extraction; UV radiation; microwaves; supercritical $CO_2$; ammonia explosion technology; osmotic filtration; and pressure filtration for sterilization.

Growth conditions such as the presence and concentration of gasses can be controlled in the growth container. For example excessive oxygen (a byproduct of photosynthesis) in the growth container can be undesirable because it can shift the photosynthesis-respiration balance to respiration and thus reduce the rate of biomass production and accumulation. Oxygen content in the growth medium can be monitored and excess oxygen can also be removed. Oxygen can be removed, for example, by passing $CO_2$ through the growth medium as scrubbing gas, scavenging oxygen with a membrane, and absorbing oxygen through reduction-oxidation reactions (e.g., with $H_2$). Note, however, that it may be desirable to allow oxygen to accumulate, or even provide oxygen to, a dark region of the growth container (e.g., the second region, discussed above).

In various embodiments, the growth container can include a system of optically transparent troughs/sluices and tanks housed within a building.

The building can be, for example, about 100 m wide, about 500 m long, and about 10 m tall. The troughs/sluices can be, for example, about 1 m wide and about 1 m deep. The troughs/sluices can be, for example, arranged side-by-side in an array running along the length of the building with about 0.5 m of space between troughs/sluices. Buildings can be shaped and sized to accommodate essentially any number or shape of troughs/sluices.

The building houses a pump system for pumping water through the troughs/sluices, to circulate the growing algae. In one embodiment, the pump rate can be about 100-1000 L/m per hour. The building also houses an array of growth lamps that provide light energy in the red wavelength to the algae in the troughs/sluices. In one embodiment the light energy can be provided at an intensity of about 10-1000 J/m2. The pump rate and/or the energy intensity can facilitate algae circulation, growth, and harvesting by preventing the algae from adhering to an inner surface of the troughs/sluices.

The building houses a temperature control system for maintaining the algae at a predetermined temperature. In one embodiment, the temperature is maintained at about 30-35° C. The building also houses one or more systems for controlling gas (e.g., CO2, O2) and/or micronutrient (e.g., fertilizer) concentration. The concentration of algae in the growth medium can be monitored and controlled, to improve the circulation and growth of the algae. For example, algae has an optimum concentration range for maintaining the algae in a flowing medium. In one embodiment, the algae flows and remains suspended best when it is present in the growth medium at a concentration of about 4-5 g/L. At higher concentrations (e.g., about 15-25 g/L), the algae can adhere to an inner surface of the troughs/sluices and can exhibit resistance to flowing though the troughs/sluices).

The building also houses one or more harvesting tanks in fluid communication with the troughs/sluices. In one embodiment, the harvesting tanks are about 5-10 m tall. The algae suspension can be pumped from the troughs/sluices into a harvesting tank, where mature algae settles in a lower portion of the harvesting tank while immature algae remains suspended in an upper portion of the harvesting tank. Accordingly, immature algae can be collected from the upper portion (e.g., about 1-2 m and higher in the harvesting tank), for continued growth in the troughs/sluices and mature algae can be harvested from the lower portion (e.g., to be de-watered and processed into a biomass feedstock).

The exemplary building described above can circulate about 100-1000 million liters of growth medium per day. Accordingly, the building can produce about 500-5000 million grams of dry biomass per day, depending upon the concentration of the circulating algae. Growing the biomass can include bioremediation. The biomass can be harvested and processed according to the methods described above to produce biomass feedstocks, fuels, and/or specialty chemicals.

While the invention has been particularly shown and described with reference to specific embodiments, it should be understood by those skilled in the art that various changes in form and detail can be made without departing from the spirit and scope of the invention as defined by the appended claims.

What is claimed is:

1. A method for producing biocrude from algae comprising:
   growing the algae in a growth container with a greenhouse gas and light energy; and
   catalytically cracking substantially all of the organic components of the algae to produce a biocrude, wherein the greenhouse gas comprises CO2 provided directly from an adjacent industrial facility; and
   wherein the algae comprises macro algae.

2. A method for producing biocrude from algae comprising:
   growing the algae in a growth container with a greenhouse gas and light energy; and
   catalytically cracking substantially all of the organic components of the algae to produce a biocrude, wherein the greenhouse gas comprises CO2 provided directly from an adjacent industrial facility; and
   wherein the growth container comprises a stirring reactor with an internal light source and reflective inner wall.

3. A method for producing biocrude from algae comprising:
   growing the algae in a growth container with a greenhouse gas and light energy; and
   catalytically cracking substantially all of the organic components of the algae to produce a biocrude, wherein the greenhouse gas comprises CO2 provided directly from an adjacent industrial facility; and
   wherein the growth container includes a sluice comprising an optically transparent region, and wherein a suspension of the algae is circulated through the sluice and the light energy is provided to the algae through the optically transparent region.

4. The method of claim 3 wherein the suspension of the algae comprises about 5% by weight micro algae in an aqueous liquid.

5. A method for producing biocrude from algae comprising:
   growing the algae in a growth container with a greenhouse gas and light energy; and
   catalytically cracking substantially all of the organic components of the algae to produce a biocrude, wherein the greenhouse gas comprises CO2 provided directly from an adjacent industrial facility; wherein the algae is dewatered, agitated and contacted with a catalyst prior to the catalytic cracking; and
   wherein the catalyst comprises acid alum and sodium silicate.

6. A method for producing biocrude from algae comprising:
   growing the algae in a growth container with a greenhouse gas and light energy; and
   catalytically cracking substantially all of the organic components of the algae to produce a biocrude, wherein the greenhouse gas comprises CO2 provided directly from an adjacent industrial facility; and further comprising flocculating the algae with a plurality of solid biomass particles.

7. The method of claim 1 wherein the growth container comprises a flexible pouch adapted for growing macro algae.

8. A method for producing biocrude from algae comprising:
   growing the algae in a growth container with a greenhouse gas and light energy; and
   catalytically cracking substantially all of the organic components of the algae to produce a biocrude, wherein the greenhouse gas comprises CO2 provided directly from an adjacent industrial facility; and
   wherein immature algae cells are added to the growth container.

9. A method for producing biocrude from algae comprising:
   growing the algae in a growth container with a greenhouse gas and light energy; and
   catalytically cracking substantially all of the organic components of the algae to produce a biocrude, wherein the greenhouse gas comprises CO2 provided directly from an adjacent industrial facility; wherein a liquid comprising sewage is introduced to the growth container and wherein algae is grown in the liquid; and wherein purified water is separated from the liquid with a one-way osmotic membrane in fluid communication with the growth container.

* * * * *